United States Patent [19]

Huch

[11] 4,217,196

[45] Aug. 12, 1980

[54] DISH-ELECTRODE CONCENTRATION METER WITH DETACHABLE TRANSDUCER

[76] Inventor: Albert Huch, Kugelgasse 1, Marburg D-3550, Fed. Rep. of Germany

[21] Appl. No.: 43,220

[22] Filed: May 29, 1979

[30] Foreign Application Priority Data

May 30, 1978 [DE] Fed. Rep. of Germany ....... 2823485

[51] Int. Cl.$^2$ ..................... A61B 5/05; G01N 27/46; G01N 31/14
[52] U.S. Cl. ........................... 204/195 B; 204/1 T; 23/230 B; 424/12; 204/195 M
[58] Field of Search ............... 204/1 T, 1 E, 195 B, 204/195 P, 180 G, 180 S, 195 M, 195 S; 23/230 B; 424/12; 128/2 E

[56] References Cited

U.S. PATENT DOCUMENTS

| | | | |
|---|---|---|---|
| 3,661,748 | 5/1972 | Blackmer | 204/195 P |
| 3,787,309 | 1/1974 | Neti et al. | 204/195 M |
| 3,896,008 | 7/1975 | Keyes | 204/1 E |
| 3,932,233 | 1/1976 | Ruzicka et al. | 204/195 M |
| 4,020,830 | 5/1977 | Johnson et al. | 204/195 B X |

Primary Examiner—Arthur C. Prescott
Attorney, Agent, or Firm—Michael J. Striker

[57] ABSTRACT

A dish-electrode concentration transducer unit of the type into whose dish one or a few drops of blood, on the order of 20-50 microliters, is dropped. The dish-defining structure of the transducer unit is thermally conductive, and both it and the transducer of the unit are thermostatically temperature-controlled, in order that the transducer and the blood being investigated be maintained at requisite temperature. The transducer is, in assembled condition of the transducer unit, held in place pressed against the thermally conductive dish-defining structure so as to be in thermally conductive engagement therewith. Accordingly, the transducer of the unit can be replaced with involvement of the heating element or temperature sensor of the thermostatic system of the transducer unit, and certainly without accompanying replacement of the temperature sensor.

5 Claims, 2 Drawing Figures

DISH-ELECTRODE CONCENTRATION METER WITH DETACHABLE TRANSDUCER

BACKGROUND OF THE INVENTION

The present invention concerns dish-electrode concentration meters and their transducers, and specifically those employed to measure the concentration of a substance of interest, usually a gas, in blood. The transducer of the meter adjoins a structure which defines a small dish, the bottom of which is formed by the transducer structure itself, and one or perhaps two drops of blood are dropped into the dish for contact with the concentration meter's actual transducer. The amount of blood involved in such a measurement is very small, on the order of about 20–50 microliters. The structure defining the little dish or pan is typically made of good thermally conductive material and is furthermore in good thermally conductive engagement with the actual transducer, in order that both the one or two drops of blood contacting the transducer and also the transducer be capable of being maintained at the temperature at which the concentration measurement need be performed.

Such a dish-electrode concentration meter is disclosed, for example, in Federal Republic of Germany published patent application DE-OS No. 23 47 779. With such constructions, the heating element, e.g., a heating coil, of the thermostatic system used to maintain required temperature is mounted on the actual transducer structure, as is also the temperature sensor of the meter's thermostatic system. There is a frequent need to replace the transducer of the concentration meter, for various reasons including wear, the need for inspection, and so forth. However, removal of the transducer then necessitates removal or disassembly of the heating element and the temperature-sensing element of the meter's thermostatic system; alternatively, the temperature sensor is non-removably mounted on the transducer structure, or is not feasably disassembled from the transducer structure, so that when the new or substitute transducer is then installed it is accompanied by a new temperature sensor whose presence, in turn, necessitates recalibration.

SUMMARY OF THE INVENTION

Accordingly it is a general object of the invention to provide a dish-electrode concentration meter of the type in question, so designed that the need for transducer replacement is not combined with excessive and awkward disassembly and reassembly work.

It is a related object of the invention that the need for transducer replacement not be combined with the need to each time recalibrate the thermostatic system of the concentration meter.

In accordance with the present invention, the transducer of the dish-electrode structure is removably mounted in the housing of the structure and is provided with means which presses the transducer structure into good thermal engagement with a thermally conductive part of the structure defining the little dish of the meter, and in particular so as to be pressed against the dish-defining structure at the side thereof opposite to the side towards which blood is dropped into the little dish.

Preferably, the structure defining the little dish furthermore defines the compartment in which the actual transducer is to be accommodated within the housing of the meter, or of the meter's transducer housing.

Preferably the transducer housing is in other respects heat-insulating, and the electrical leads which connect the actual transducer to the meter's power supply and to its indicator are fed out of the transducer housing through the insulating material of the transducer housing.

According to a further concept of the invention, the concentration transducer is mounted on a base plate, and the base plate is provided with means for pressing the transducer into good thermally conductive engagement with the thermally conductive dish-defining structure.

A particular advantage of this latter feature, for example in the case of oxygen-concentration transducers, is that when their membrane is to be stretched over and clamped into the transducer structure, this can be performed on the base plate, quite conveniently and definitely before inserting the base plate and transducer into place in the transducer housing. In general, the use of such a base plate facilitates removal and replacement of transducers, irrespective of the specific type of concentration transducer involved.

In particular, the use of means which merely press the transducer into the requisite thermally conductive engagement, e.g., tightened screws provided on a somewhat elastic base plate, makes it possible to install a new transducer with extreme quickness and simplicity.

According to another feature of the invention, the structure defining the little dish or shallow basin into which the drops of blood are dropped exhibits an inclination in the range of between 5° and 25°. It has been found that this very greatly facilitates cleaning of the measuring surfaces involved. In the prior art, considerably steeper angles of inclination were employed, and were relied on to develop above the thin bottommost layer of blood which actually contacts the transducer protective higher layers of blood to protect the actually measured blood from the ambient atmosphere, to which the little bit of blood in the little dish is in other respects freely exposed. However, it has been found that the use of shallower inclination angles for the dish, which are so advantageous in terms of maintenance and service, do not detract from the operativeness and accuracy of the meter.

Because the electrical leads connecting the transducer to the power-supply and indicator of the meter are fed out through the heat-insulating transducer housing, the latter can readily be made a part of the housing for the power supply and indicator. This results in a one-piece or one-housing meter unit which is readily serviced and very conveniently stored.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF PREFERRED EMBODIMENTS

Figure 1:
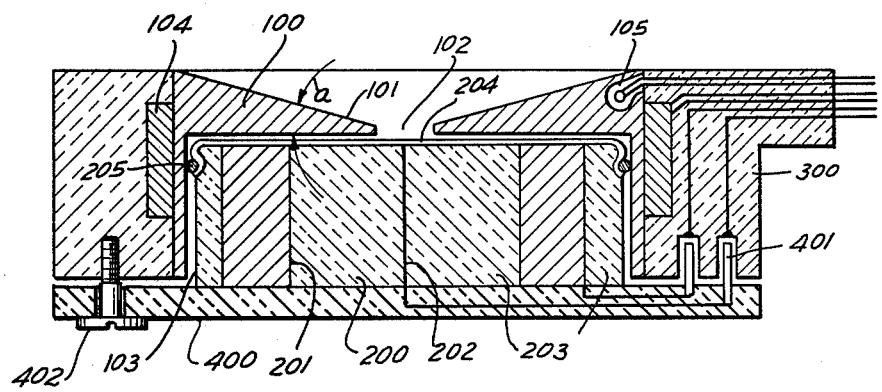
FIG. 1 is a cross-section taken through the concentration transducer and transducer housing of the dish-electrode concentration meter.

In FIG. 1, numeral 100 denotes the dish-defining structure of the dish-electrode meter. Its upward facing conical surface 101 defines the little dish into which drops of blood are dropped and is provided with a central aperture 102, in which the one or few drops of blood are to collect. The angle of inclination a of the dish-defining surface 101 is between about 5° and 25°, in contrast to the considerably steeper angles hitherto used in the prior art. The dish-defining structure 100 is made of a good thermally conductive material, such as copper or aluminum but not limited thereto. The dish-defining structure 100, at its lower side, defines a compartment 103 which is to accomodate the actual concentration transducer 200 of the meter.

Numeral 104 denotes the heating coil of the meter's thermostatic temperature-regulating system, and is wound around the dish-defining structure 100 of the transducer unit. Numeral 105 denotes the thermostatic system's temperature sensor, and as can be seen the sensor 105 is mounted on or in the thermally conductive dish-defining structure 100. Accordingly, neither the heating element 104 nor the temperature sensor 105 are involved, when the concentration transducer 200 is removed from the transducer unit. The remainder of the thermostatic system is not expressly illustrated, but serves in the conventional way to maintain the blood dropped into the dish at the temperature required for the concentration measurement.

Here, by way of example, the concentration transducer 200 has the form of a polarographic oxygen-concentration transducer, but it will be understood that other forms of concentration transducer might equally well be involved. The oxygen-concentration transducer 200 here shown comprises a conventional reference electrode 201 and one (or more) conventional measuring electrodes 202. Both the measuring electrode 202 and the annular reference electrode 201 surrounding it are encased in a body of electrically insulating material. Stretched across the top surface of the structure 201, 202, 203 is a permeable membrane 204. The membrane is held in place, stretched over the top of the structure as shown, by means of a clamping or tension ring 205 which presses the edge of membrane 204 seal-tightly into a peripheral groove located at the upper end of electrically insulating body 203. In the usual way, a body of electrolyte is confined between the lower face of the membrane 204 and the upper face of the structure 201, 202, 203, although the body of electrolyte is not shown, to avoid crowding in the drawing.

Numeral 300 denotes the main part of the housing for the concentration transducer 200 or 201-204. The transducer housing 300 is made of thermally insulating, and also electrically insulating material, such as ceramic material but not limited thereto. The inner peripheral wall of transducer housing 300 has an annular recess, in which heating coil 104 is accommodated, and the balance of the inner peripheral wall of transducer housing 300 accommodates and mounts the dish-defining structure 100 of the transducer unit.

The transducer 201-204 is carried on a base plate 400 made of preferably thermally and electrically insulating material. In the illustrated embodiment, the transducer 201-204 is fixedly secured to the base plate 400, e.g., by means of cement, but alternatively the transducer could merely rest on base plate 400, for example with the latter having an annular depression or raised annular ledge, or the like, for properly positioning the transducer 201-204.

One or more screws or threaded bolts 402 (only one shown) pass through apertures in the base plate 400 and are screwed into threaded bores at the bottom face of the transducer housing 300. In this way, when the screws 402 are in tightened condition, the transducer 200 is pressed into good thermal engagement against the thermally conductive material of the heated dish-defining structure 100. Advantageously, the vertical length of the transducer is slightly longer than the vertical length of the compartment 103 accommodating it, and also the base plate 400 can be made of somewhat elastic material, in order to maximize the pressing force with which the transducer 200 is pressed into engagement with dish-defining structure 100.

The electrical leads for the heating element 104 and for the temperature sensor 105 pass through the insulating material of the transducer housing 300 to the outside thereof.

In the illustrated embodiment, the electrical leads for the reference electrode 201 and for the measuring electrode 202 pass through the insulating material of the base plate 400 and terminate at male plug connectors 401 which are embedded into the material of the base plate 400. The male plug connectors 401 are conductively engaged in female plug connectors embedded in the material of transducer housing 300, from which extend leads through the material of transducer housing 300 to the exterior thereof. The connectors 401 employed are, for example, gold-plated connectors, but it will be understood that quick-connect, quick-disconnect connectors other than of the male-and-female type shown could of course be employed. The various leads extending out from the transducer housing 300 at the upper right thereof as shown, lead to the concentration meter's power supply and indicator, not shown in FIG. 1. In the usual way, the thermostatic system of the meter maintains both the dish-defining structure 100 and the transducer itself at a constant temperature, e.g., body temperature.

Accordingly, in the illustrated embodiment, when one transducer 200 (201-204) is to be removed and replaced by another, of the same or differing type, it is merely necessary to loosen the threaded bolts 402, whereupon both the transducer 200 and the base plate 400 to which it is secured pull out, the male-and-female electrical connectors 401 disengaging in the process. The new transducer, with its own base plate 400, is then inserted, the bolts 402 reinserted and tightened, and a concentration measurement can then be immediately performed, without awkward or skillful disassembly and reassembly work being involved, and without any need to recalibrate the meter's thermostatic system for a new temperature sensor 105, the same temperature sensor 105 being again used.

Figure 2:
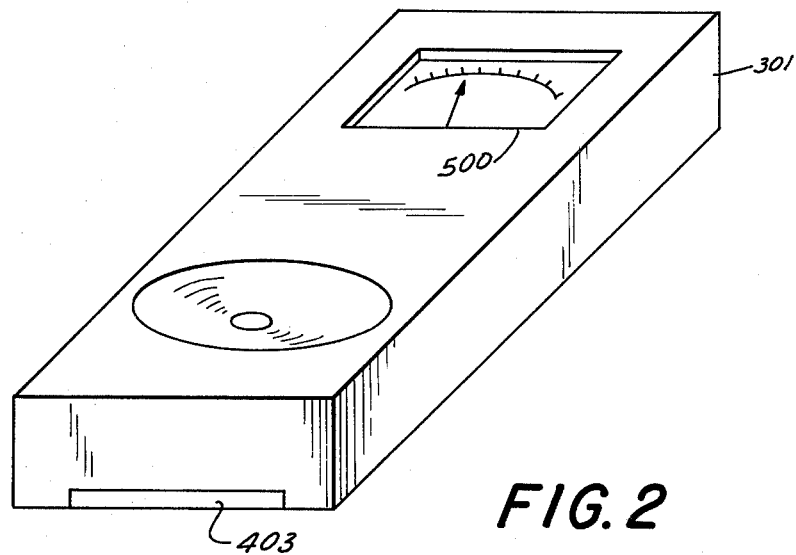
FIG. 2 depicts a concentration meter provided as a one-housing unit with the transducer housing incorporated therein.

Because of the manner in which the transducer 200 (201-204) of FIG. 1 can, with its base plate 400, be quickly and easily removed from the transducer housing 300, it becomes feasible to structurally integrate the transducer housing 300 with the housing for the meter's indicator, and also its power supply if it has a power supply of its own. This is shown in FIG. 3, where the housing 301 of a one-housing concentration meter is of one piece with, e.g., a single piece of material with, the transducer housing corresponding to 300 in FIG. 1. Numeral 500 denotes the meter's indicator. Numeral 403 denotes, at the bottom of the meter, a small lid or door which can swing or slide open, to expose the base plate 400 of FIG. 1 and the mounting bolts 402 for transducer removal; alternatively, the base plate 400 itself can be located where door or lid 403 is shown in FIG. 2, with the mounting screws 402 being uncovered at the underside of the housing 301 of the meter.

It will be understood that each of the elements described above, or two or more together, may also find a useful application in other types of constructions differing from the types described above.

While the invention has been illustrated and described as embodied in a dish-electrode concentration meter employing a polarographic oxygen-concentration transducer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An improved dish-electrode concentration transducer unit of the type including a dish-defining structure of thermally conductive material forming a dish into which a quantity of blood on the order of 20–50 microliters is dropped and including a concentration transducer, the improvement comprising a transducer housing of insulating material accommodating the thermally conductive dish-defining structure and forming a transducer compartment in which the transducer is accommodated; means pressing the concentration transducer into thermal engagement with the thermally conductive material of the dish-defining structure; quick-disconnect electrical connectors on the transducer housing for electrically connecting the concentration transducer to a power supply and to an indicator unit and including leads connected to the quick-disconnect electrical connectors and extending away from the transducer housing.

2. The transducer unit defined in claim 1, furthermore including a base plate, the concentration transducer being carried on the base plate, the pressing means being provided on the base plate.

3. The transducer unit defined in claim 1, the dish-defining structure having a dish-defining surface exhibiting an inclination of between about 5° and 25°.

4. The transducer unit defined in claim 1, furthermore including an indicator unit for indicating a concentration reading, the housing accommodating both the transducer and the indicator.

5. The transducer unit defined in claim 1, the transducer unit including a heating element and a temperature sensor not mounted on the transducer, whereby removal of the transducer from the transducer housing does not involve the heating element and temperature sensor, the heating element and temperature sensor instead being mounted to heat and sense the temperature of the dish-defining structure of the transducer unit.

* * * * *